United States Patent [19]
Pouletty et al.

[11] Patent Number: 5,147,780
[45] Date of Patent: Sep. 15, 1992

[54] MULTIWELL STAT TEST

[75] Inventors: Philippe Pouletty, Redwood City; Beth Atwood, San Bruno; David Rommler, Woodside, all of Calif.

[73] Assignee: Sangstat Medical Corporation, Menlo Park, Calif.

[21] Appl. No.: 644,941

[22] Filed: Jan. 23, 1991

Related U.S. Application Data

[62] Division of Ser. No. 444,814, Dec. 1, 1989.

[51] Int. Cl.⁵ .......................................... G01N 33/536
[52] U.S. Cl. ...................................... 435/7.1; 435/7.9; 435/971; 436/514; 422/58; 422/61
[58] Field of Search ................................ 422/56–58, 422/61; 435/7.1, 7.5, 7.94, 7.9; 436/514

[56] References Cited

U.S. PATENT DOCUMENTS

| | | | |
|---|---|---|---|
| 4,752,448 | 6/1988 | Wells et al. | 422/66 |
| 4,948,561 | 8/1990 | Hinckley et al. | 422/61 |
| 4,978,504 | 12/1990 | Nason | 422/61 |

*Primary Examiner*—Christine Nucker
*Assistant Examiner*—Jeffrey Stucker
*Attorney, Agent, or Firm*—Bertram I. Rowland

[57] ABSTRACT

An apparatus is provided for the detection and semi-quantitative measurement of analytes. The assay results are visualized by the formation on a filter of a colored annular or circular spot, the diameter of the spot being related to the concentration of the analyte of interest. The filter on which the assay results are visualized is divided into multiple regions by strips of non-porous tape crossing the filter surface. The invention also includes a component for diluting sample to a suitable concentration for analysis, and dispensing the diluted sample onto the test filter.

4 Claims, 3 Drawing Sheets

MULTIWELL STAT TEST

This is a divisional application Ser. No. of 07/444,814, filed Dec. 01, 1989, now abandoned.

INTRODUCTION

1. Technical Field

The field of this invention relates to assay devices employing an immobilized specific binding pair member and for collecting, diluting and dispensing clinical specimens.

2. Background

Many immunoassay procedures have been devised for the purpose of detecting specific analytes. Such assays have found countless applications as tools in medicine. Analyte specific assays have been used to detect antibodies produced in response to infection, components of pathogenic agents, levels of drugs, hormones, and enzymes, etc. In addition to medicine, immunoassays and other related assays have also found numerous applications in manufacturing industries, for example, the detection of food contaminants.

Heterogeneous immunoassays usually involve a ligand or antibody immobilized to a solid support. A sample containing the analyte of interest is passed over the immobilized immunoreagent and the amount of antibody-ligand complex formed is measured. In heterogenous assays, essential elements include the anchoring of one member of a specific binding pair to a solid support, and a means for either directly or indirectly detecting label bound to the support.

The ease of performing an assay procedure is always an important consideration. Most assays involve the addition of multiple reagents and require multiple washing steps. Ideally, an assay will be simple and not require the use of complex equipment such as microtiter plate washers or ELISA readers. Immunoassays able to be performed in a physician's office, at home, or in the field are of particular interest and must be developed to be performed without the use of specialized equipment.

Numerous immunoassays exist in which the results are visualized by the formation of a colored spot. The intensity of the color of a spot is usually proportional to the concentration of analyte in the sample and requires instrumentation to relate the color intensity to analyte concentration. Otherwise, with visual comparison of the color intensity of spots produced by different samples may be an uncomfortably subjective exercise. Even with semiquantitative assays, differences may be only difficultly distinguished. Furthermore, analysis of test results that exclusively rely on color changes may be exceptionally difficult when weakly positive results are obtained. There is therefore interest in providing semiquantitative assays which have simple protocols, and substantially reduce subjective error associated with the determination of a positive result and the amount of analyte.

3. Relevant Literature

U.S. Pat. Nos. 4,727,019 and 4,632,901 relate to immobilized phase immunoassay devices that produce a colored spot when exposed to a sample containing appropriate analyte for detection.

SUMMARY OF THE INVENTION

Methods and apparatus are provided for performing a non-instrumental assay for the detection of an analyte in a liquid sample. The apparatus comprises a porous reactive filter, a porous separation layer, a non-porous flow control layer and an absorbent waste fluid receiving layer. The reactive filter comprises a specific binding pair member distributed in a radial non-linear concentration gradient. A circular or annular shaped spot is produced on the porous reactive filter, where a small diameter spot indicates analyte concentration below a predetermined level.

A sample preparation apparatus is also provided that serves as a collector-diluter-dispenser comprising a cap enclosed tube. The collector-diluter-dispenser device absorbs sample by means of a nib. The collector-diluter-dispenser contains a liquid medium restrained from the nib by a frangible barrier which supports the nib, with the nib extending through an opening in the cap. After absorbing the sample with the nib, breaking the barrier drops the nib into the liquid medium and the sample dissolves into the liquid medium. Exerting pressure on the sides of the collector-diluter-dispenser permits the diluted sample to be dispensed through the opening originally containing the nib and onto the assay apparatus.

DESCRIPTION OF THE DRAWINGS

The invention will be better understood by reference to the following detailed description of specific embodiments when considered in combination with the drawings that form part of this specification, wherein.

DESCRIPTION OF SPECIFIC EMBODIMENTS

Figure 1:
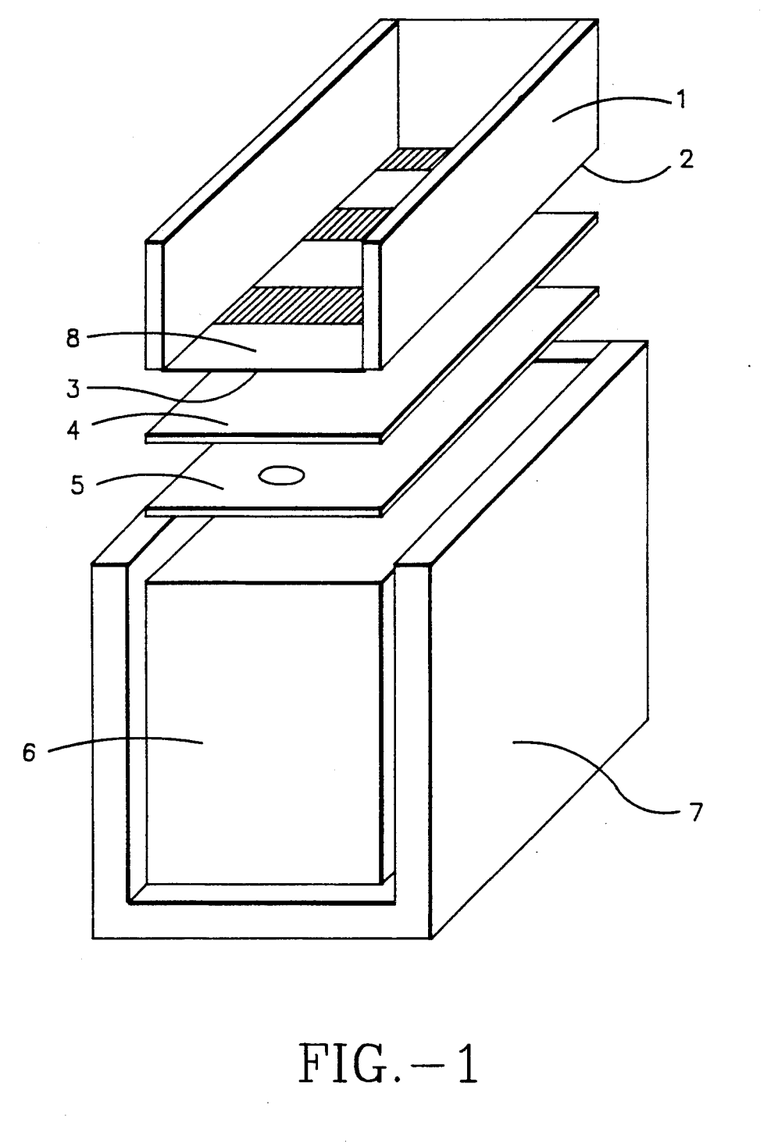
FIG. 1 is an obliquely positioned perspective view of an assay apparatus.
Figure 3:
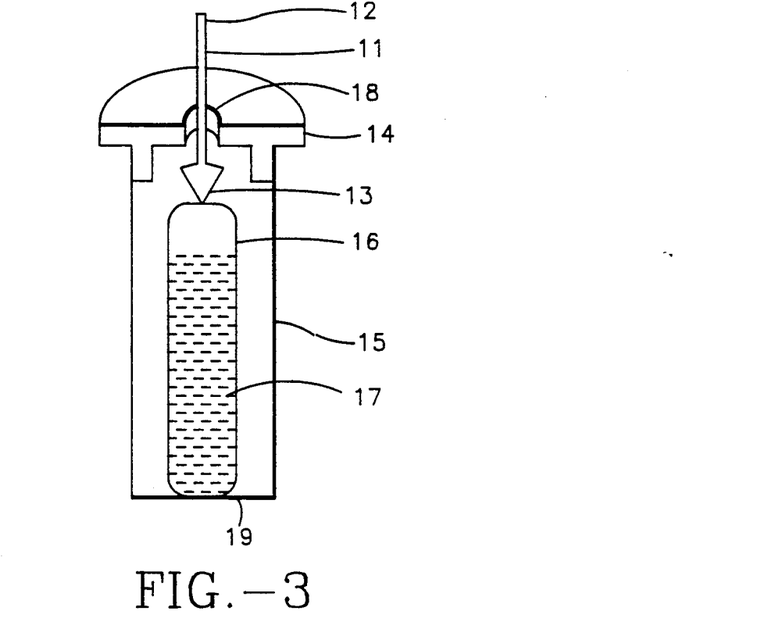
FIG. 3 is an elevational cross-sectional view of the collector-diluter-dispenser apparatus.
Figure 4:
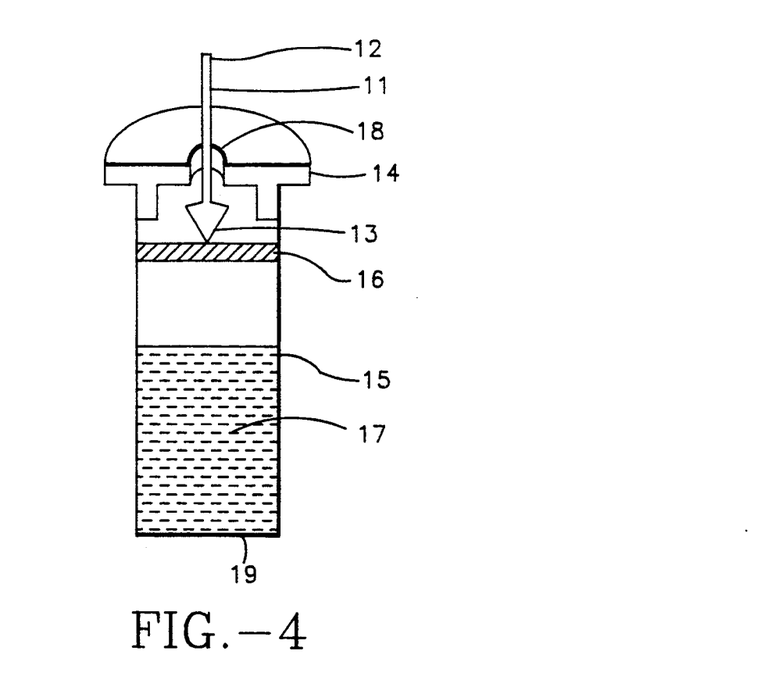
FIG. 4 is an elevational cross-sectional view of an alternate embodiment of the collector-diluter-dispenser apparatus of FIG. 3.

The system of the subject invention comprises two principal components. The first component as shown in FIG. 1 is an apparatus for assaying the presence of an analyte of interest. The second component as shown in FIGS. 3 and 4, consists of a device for diluting sample and dispensing the diluted sample. The second component can be used to apply the diluted sample to the assay apparatus.

The assay apparatus of FIG. 1 is used to detect the presence of an analyte in a sample. The assay apparatus is able to semi-quantitatively measure the amount of the analyte found in the sample. Analytes suitable for detection in the assay apparatus are members of specific binding pair members. Specific binding pairs are defined as two non-identical molecules capable of specifically and usually non-covalently binding to each other in solution so as to form stable complexes that can be detected either directly or indirectly. Exemplary but not exclusive of general classes of specific binding pair interactions are ligand-receptor interactions, which are primarily exemplified by antibody-hapten or antibody-antigen interactions. Ligands for the most part will be non-proteinaceous, naturally occurring or synthetic organic molecules of from about 125 to 5,000 Dal, and peptides and proteins. Receptors that may be detected by the subject apparatus will for the most part be proteins, such as immunoglobulins, fragments thereof, particularly monovalent fragments, of immunoglobulins, e.g., Fab, Fv, etc., enzymes, naturally-occurring receptors, e.g., T-cell receptors, hormone receptors, surface membrane receptors, lectins, etc. Other specific binding pairs include nucleic acids, e g., DNA and RNA. For a disclosure of specific ligands and receptors see U.S. Pat. No. 3,996,345, columns 10-17, which disclosure is hereby incorporated by reference.

Results from assays performed with the subject apparatus are visualized as an annular or circular spot formed on a filter. The spot for a positive result has a dark central region and a lighter exterior region. Differences in concentration can be detected by having a dark central ring or both the central dark ring and a colored outer ring. As detected in the subject invention, the correlation between the diameter of the result and indicator spot and the analyte concentration provides significant advantages. By providing for a small high intensity spot for analyte within a predetermined concentration, and a larger, less intense spot above such concentration visual detection can give a reasonable estimate of the amount of analyte, particularly whether below or above a threshold value.

The correlation between the diameter of the indicator spot and the concentration of analyte is achieved by immobilizing a binding pair member to the porous filter in a non-linear radial concentration gradient, which may be the same compounds as the analyte, a cross-reactive compound, or a reciprocal binding pair member. The term "reciprocal binding pair member" is intended to mean the member of a specific binding pair which complexes with the designated member, frequently in reference to the analyte as the designated member. The radial concentration gradient is arranged so that the highest concentration of the specific binding pair member is at the inner region of a ring, having a relatively small diameter relative to a second concentric ring comprising a lower concentration per unit area of the same binding pair member. Usually the central ring will have a diameter in the range of 0.1 to 0.5:1, usually 0.1 to 0.3:1 as compared to the diameter of the outer ring.

As shown in FIG. 1, the assay apparatus contains multiple layers, arranged in a specific order and held together in register by a housing 7. The assay apparatus has four principal layers. The layers will usually be of essentially the same circumferential dimensions, e.g., length and width, but may vary with respect to one another as to the thickness. The principal layers, in descending order, are as follows. The top layer is a porous reactive filter 3, which may be divided into regions by a non-porous divider, e.g., tape 9; at least one of the regions, usually all or most of the regions, contain at least one specific binding pair member ring 10 capable of forming complexes related to the analyte. Beneath and contacting the filter layer is a porous separation layer 4. Below the porous support layer is a flow-rate control layer 5. The bottom layer is a waste fluid receiving absorbent pad 6. The porous separation layer 4, the flow rate control layer 5, and the waste fluid receiving pad 6, may be excluded, but will normally be present.

By reactive in referring to the porous reactive filter, it is intended that immobilized to this filter is a specific binding pair member capable of binding the analyte or its reciprocal binding member. The porous reactive filter may be composed of paper, cellulose, glass fiber, nylon, PVDF, or the like. Preferably the filter will be comprised of nylon. Commercially available examples of such filters include Immobilon (Millipore), Memtest membrane (Memtek), Biodyne (Pall), Immunodyne (Pall), and Ultrabind (Gelman Sciences). The pores in the porous reactive filter will have an average diameter in the range of about $0.1\mu$ to $10\mu$, usually in the range of about $1\mu$ to $7\mu$.

Figure 2:
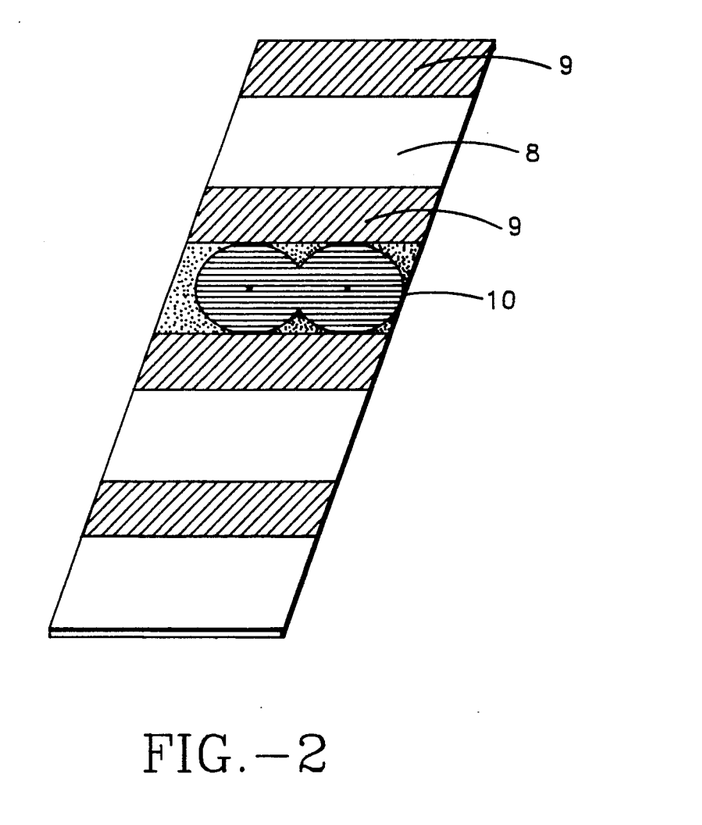
FIG. 2 is a plan view of the porous reactive filter of the apparatus of FIG. 1.

The porous reactive filter 3 may be divided into a plurality of regions, conveniently separated by non-porous dividers, e.g., tape 9. The different regions may serve different functions, for example, providing for different concentration ranges of the specific binding pair member or different binding pair members for panel test applications. A control may have a predetermined amount of label or be free of any binding pair member or the like. All or a portion of the region may contain the specific binding pair member. The regions will conveniently be in the range of from about 3 to 50 $mm^2$, usually 4 to 14 $mm^2$. The non-porous tape can provide a color contrast with the regions, preferably being white or yellow to enhance the colored appearance of a positive result. The separation between regions provided by the tape will generally be about 0.2 to 15, usually 1 to 4 mm.

A member of the specific binding pair either binding to or cross-reactive with analyte is applied and becomes non-diffusively bound or immobilized to a porous filter so as to generate a circular spot or ring with a non-linear radial concentration gradient that has a substantial drop in concentration at a relatively short distance from the center of the ring, generally dropping by at least about twenty five percent within a band of about 0.5 mm width from the average concentration of the central region. The filter material employed is desirably, but not necessarily, chemically reactive so as to covalently bond the specific binding member. By appropriate application of the binding pair member solution, a high concentration of binding pair member can be obtained in a small radius from the center surrounded by a concentric contiguous outer circle of larger radius and substantially lower concentration.

The application solution will normally be a buffered solution at a pH in the range of about 4 to 10 with a concentration of specific binding pair member of about 10 $\mu$g/ml to 5 mg/ml. Other solutes may include salt at a concentration in the range of about 10 $\mu$M to 1 M. By lowering or increasing the buffer concentration or adding other unreactive solutes, e.g., glycols, the rate of diffusion of the specific binding pair member may be modified to increase or decrease the diameter of the high concentration region.

The high concentration region is achieved by virtue of the high reactivity of the porous filter, compression in the region about the site of application of the solution and depletion of the specific binding pair member from the solution in the central region.

The nib can be applied to the porous reactive filter at a pressure which modifies the porosity of the membrane in the depressed area, so as to be sufficient to produce a ring of binding pair member about an uncolored center, rather than a completely filled circle.

Different binding pair members may be applied to different regions so that the presence of multiple analytes in a single sample may be simultaneously analyzed. The same binding pair members at different concentrations may be applied to different regions so as to aid in the quantitative determination of the analyte concentration and provide for a wider range of detectable analyte concentrations on a single or subdivided porous reactive filter or the individual regions may be independent filter elements. One or more spots of the same binding pair member may be applied per region, normally at the same concentration. When more than one binding pair member spot is present in a single region, the spots may be overlapping. In a preferred embodiment of the invention, two binding pair member spots will be present in each measurement region. One or more regions may not contain a binding pair member so as to provide a negative control. Positive controls may also be provided for analyte by providing for the presence of a predetermined amount of label.

A porous separation layer 4 is located immediately beneath, directly contacting, and in register, with the porous reactive filter layer 3 of the assay apparatus. The porous separation layer 4 is in contact with the lower surface of the porous reactive filter 3. The porous separation layer serves to support the porous reactive filter and permit reagents to flow uniformly from the top layer down to lower layers of the assay apparatus. The porous separation layer may be made of any rigid or semi-rigid porous material that does not substantially bind or interact with reagents used in conjunction with the invention. Exemplary of materials for the porous separation layer are fiberglass, paper, hydrophilic polypropylene, and cellulose, preferably the porous separation layer is made of H-HDC (Pall). The porous separation layer is of essentially the same circumferential dimensions or shape as the porous reactive filter layer or the elements thereof. The thickness of the porous separation layer will generally be in the range of about 0.1 mm to 1 mm.

Immediately beneath and contacting the porous separation layer 4, is flowrate control layer 5. Conveniently, the flowrate control support layer 5 contains a plurality of small uniformly placed, linearly, or randomly, arranged perforations, generally in one or two lines, preferably having the perforations below each region. The flowrate control layer serves to both slow and direct the flow of reagents through the porous reactive filter 3. The flowrate control layer 5 may be made from any non-porous wettable material that is substantially inert to the reagents employed in the performance of an assay. The flowrate control layer will be of essentially the same circumferential dimensions or shape as the filter layer. The precise thickness of the flowrate control layer is not essential to the function of the subject invention, generally ranging from about 2 to 10 mils.

The perforations will be of a size and number which serve to impede the flow of liquid reagents through the apparatus. In general, the greater the desired time of contact between the porous reactive filter and the reagents, the smaller the cross-sectional area of the perforations will be. The shape of individual perforations is not important. Individual perforations will usually have a cross-sectional area in the range of about 5 mils to 50 mils, more usually 7 mils to 15 mils with the number of perforations being about 1 to 10 per cm along the length of the flowrate control layer. The holes may be uniformly distributed so as to permit a uniform flow of reagents through the different porous regions of the porous reactive filter layer 3. It is preferable, though not essential, that the perforations in the flowrate control layer be located beneath the tape free regions of the porous reactive filter 3.

Below and directly contacting the flowrate control layer 5, is a waste fluid receiving layer 6. Reagent solution flowing through perforations in the flow rate control layer directly enter the waste fluid receiving layer. The waste fluid receiving layer draws reagent solutions away from the other layers of the assay apparatus. The absorbing volume of the waste fluid receiving layer is substantially greater than the total volume of reagents required to be added to the assay apparatus for the performance of a given assay. The waste fluid receiving layer may be of any convenient material, such as cotton, blotting paper, polyester fibers, cellulose acetate, or the like.

The multiple layers of the assay apparatus are held together in an apparatus housing 7. The housing will be made of an inert material conveniently being any of a variety of commercial plastics which may be molded, for example, polyethylene, polypropylene, styrene, ABS, polyacrylate, polystyrene, or the like.

FIG. 1 illustrates one possible embodiment of such a housing. The housing is capable of compressing the layers to maintain continuous and uniform contact between the layers of the apparatus so that liquid flowing through the apparatus will flow uniformly through the porous reactive filter 3. The housing may consist of one or more pieces. Preferably, the housing will consist of two pieces, an upper reservoir 1, and a lower casing 7. The reservoir 1 is the top portion of the housing and may have an inner lip to maintain the layers under compression. For convenience, the reservoir may be separable from the rest of the housing.

The reservoir may be partially or completely filled with the diluted sample, so that diluted sample is uniformly distributed over the filter surface. The reservoir may contain marking lines that indicate the amount of solution added. The reservoir has an open bottom 2 and is enclosed at the bottom with porous reactive filter 3. The apparatus may be marked so as to distinguish one end of the apparatus from the other. The markings may be inherent in the shape of the housing by making the housing asymmetric along at least one axis, or the polarity markings may be manifested as symbols present on the housing.

The precise dimensions of the housing are not essential to the function of the assay apparatus, but in general, the apparatus will be of a size convenient for transport, manipulation, and assembly. The housing will generally have a length in the range of about 0.5 to 5 cm, preferably in the range of about 2 to 5 cm. The width will be in the range of about 0.3 to 3 cm, preferably in the range of about 0.5 to 1 cm. Preferably, the width will be about 9 mm so as to allow batch testing using a standard laboratory multichannel micropipetter. The height of the housing will be in the range of about 0.5 to 5 cm, preferably in the range of about 1 to 3.5 cm.

A collector-diluter-dispenser apparatus depicted in FIGS. 3 and 4 may be used either in conjunction with, or independently of, the first component of the subject invention, the assay apparatus (FIG. 1). The collector-diluter-dispenser apparatus comprises five principal components: a hydrophilic nib 11, a cap 14 for retaining the nib from falling out of the collector-diluter-dispenser apparatus, a flexible tubular container 15, enclosed by cap 14, liquid medium 17, and a frangible barrier 16 restraining the flow of the liquid medium and supporting the nib from falling into the liquid medium, while the nib 11 extends through an aperture 18 in the cap 14.

The use of the collector-diluter-dispenser is described as follows. Liquid sample is contacted with the nib 11 of the collector-diluter-dispenser. Once the sample has been absorbed by the nib, the nib is withdrawn from the sample source, and the nib end of the collector-diluter-dispenser is pointed upwards. The frangible barrier 16 within the device is broken, and the breaking of the barrier 16 allows the sample containing nib 11 to fall into the liquid medium 17 where the sample is released from the nib 11 and dispensed into the liquid medium 17. The nib is capable of absorbing molecules, particles, e.g., virus particles, cells, etc., and effectively dispersing them into the liquid medium. After the liquid medium and sample have mixed, thus diluting the sample, the collector-diluter-dispenser is used as a dropper to dispense the diluted sample into the previously described assay apparatus. The collector-diluter-dispenser may be used as a dropper because the main tube 15 is made from a flexible material that deforms under pressure, and diluted sample is free to flow through an aperture 18 in the cap through which the nib 11 had previously extended.

The nib 11 serves several functions. The nib is able to absorb sample, and also release the absorbed sample into the liquid medium 17. The nib can also absorb proteins and cells for release into the liquid medium 17. Furthermore, the nib has a measuring function. Essentially identical nibs will be able to take up and release reproducible quantities of sample so that pre-determined dilution ratios may be reproducibly attained.

The nib 11, may also serve an active role by providing for various reagents. The nib 11 may also include in dehydrated form, specimen or analyte reactive compounds such as anti-coagulants (EDTA, citrate, heparin), detergents, etc. The nib 11 may also contain attached ligands in dehydrated form so that the nib 11 may serve as a solid phase support for ligand analyte interactions.

Once the nib 11 has been used to collect sample, the sample may be allowed to dry on the nib 11 prior to the release of the sample into the liquid medium, or the sample containing nib may be mixed with the liquid medium before substantial drying can take place.

The nib 11 will usually be composed of a hydrophilic relatively deformable resistant material that will be substantially inert to the analyte of interest. The nib is made of a hydrophilic material so that an aqueous sample will be drawn up the nib when the nib is touched to a fluid sample. Exemplary, but not exclusive of material suitable for the nib are nylon, polyethylene, or polypropylene. Preferably the nib material is nylon. Preferably the nibs are Nib 99356 produced by American Filtrona. The nib is essentially cylindrically shaped with the exposed end of the nib being pointed. The pointed end 12 of the nib is contacted with the sample to be analyzed. The opposing end of the nib has a bulbous shape 13 having a diameter somewhat larger than the diameter of the aperture 18 of the cap 14.

The nib will usually have a length of about 3 mm to 4 cm and a diameter of about 0.2 to 3 mm, depending on the sample size to be employed.

The cap 14 is mounted onto a flexible tube 15 sealed on one end 19. The flexible tube is made of a material that readily deforms under squeezing. Exemplary of materials for the tube are plastics such as polyethylene, polypropylene, or other inert elastomeric materials. The precise dimensions of the tube are not critical, the tube conveniently having a volume of about 1 to 5 ml.

The barrier 16 is made of a frangible material, preferably glass or plastic, and is of a thickness such that it is easily broken under hand pressure. The material should be inert to both the liquid medium and the sample.

There are many possible configurations of the barrier 16 that permit it to both support the nib and restrain the flow of liquid medium. Two possible configurations are given in FIGS. 3 and 4. In FIG. 3 the barrier 16 is the top of an ampoule containing the liquid medium. In FIG. 4 the barrier 16 is a disk extending completely across the flexible tube.

The composition of the liquid medium 17 will vary in accordance with the requirements of specific assays. In general, the liquid medium will be an aqueous solution. The liquid medium 17 may also contain compounds that have functions in the assay other than serving to dilute the sample. For example the liquid medium may contain buffers and/or non-specific binding blocking agents, e.g., bovine serum albumin, casein, serum, etc. Liquid medium 17 may also contain a specific binding pair member that may bind to an analyte contained in the specimen or a chromogenic reagent.

The subject invention may be used with established immunoassay procedures requiring the use of an immobilized phase. The use of the term "immunoassay" is meant to comprise both immunoassays and assays of similar design using immobilized specific binding pair members, even though neither member of the binding pair is an antibody or fragment thereof. These procedures involve the addition of a variety of reagents to detect the formation of specific binding pair complexes. The formation of binding pair complexes will usually be detected by the presence of a dye or fluorophore, which may be conveniently produced as a product of an enzyme mediated reaction. The labeled reagent is able to bind to binding pair complexes immobilized on the filter. Addition of suitable chromogenic reagents allows the enzyme label to reveal the location of the immobilized binding pair complexes by coloring the porous reactive filter.

The amount of sample and assay reagents added to the assay apparatus via the reservoir varies with different embodiments of the subject invention. The reservoir may be filled to the top with diluted sample and reagents, or lesser quantities may be added. In general, for a given specific embodiment, a predetermined and reproducible quantity of diluted sample will be added, while reagents will normally be present in excess. The volume of diluted sample may be measured in drops from the collector-diluter-dispenser apparatus or by a marker in the reservoir. One or more drops of diluted sample may be applied to each tape-free region, or the reservoir may either be filled partially or completely. Preferably the reservoir will be filled with diluted sample and reagents so that uniform contact between the solution and the measurement regions is maintained. Increasing the amount of diluted sample and reagent added to the reservoir will increase the contact time between the added solution and the porous reactive filter as well as the amount of specific binding pair member which binds to the surface.

The following is an example of using the subject invention to assay blood for the presence of antibodies to HTLV-1. The amount of reagents used will vary in accordance with the size of the apparatus. A drop of blood obtained by a finger prick of a patient is placed on a glass slide. The tip of the nib 11 on the collector-diluter-dispenser is touched to the blood drop on the slide (or may be directly touched to the pricked finger) and blood is drawn up the nib. When the nib is saturated, the collector-diluter-dispenser is then placed upright so that the cap 14 is on top. The frangible barrier 16 is broken by exerting pressure on the walls of the collector-diluter-dispenser. The nib falls into the liquid medium 17 and the collector-diluter-dispenser is then agitated to ensure proper mixing.

Several drops of diluted sample are then added to the reservoir on top of the assay apparatus so as to cover the reactive filter 3. The porous reactive filter contains spots of HTLV-1 envelope antigen in a non-linear radial concentration gradient bound to one or more of the measurement regions; positive and negative controls are also present where a known amount of label is present and no label is present, respectively. Immediately prior to the addition of diluted sample to the reservoir, a solution of blocking agent is added to the reservoir and the reservoir is allowed to drain. By blocking agent it is intended a solution containing a compound or compounds, e.g., bovine serum albumin or casein, that will block any non-specific binding sites available on the porous reactive filter. After addition of the diluted sample, the diluted sample is allowed to drain. A solution of biotinylated goat anti-human IgG antibodies are then added to the reservoir and the solution allowed to drain. A solution containing streptavidin conjugated alkaline phosphatase is then added to the reservoir and allowed to drain. A wash solution buffer is then added to the reservoir and allowed to drain. A solution containing a chromogenic alkaline phosphatase substrate is then added to the reservoir and allowed to drain. After color has developed, a reaction stop solution (0.2 M phosphate pH 6) is added to stop the enzyme reaction.

It is evident from the above description that the subject invention provides apparatuses and methods for performing a wide variety of assays suitable for the detection and measurement of analytes in many types of sample. The presence of an analyte is manifested by the formation of a colored spot. Once the concentration of analyte in a sample is above a predetermined threshold, the diameter of the colored spot increases to define a larger diameter circle. The correlation between analyte concentration and spot diameter constitutes a significant advantage over immunoassays in which the results are conveyed simply by means of changes in color intensity. Another advantage of the subject invention is the formation of a ring pattern, the combination of ring pattern formation and color formation being much easier to recognize than just the formation of a simple colored spot; this advantage is especially important when the color is of low intensity. Interpreting changes in color intensity requires complex optical instruments, or reliance on crude estimates. Since the subject invention does not require complex equipment, assays may be performed in environments such as a physician's office or the field, thus providing for significant savings in both cost and time.

The subject invention also provides for a collector-diluter-dispenser apparatus that accurately dilutes a quantity of sample to a predetermined ratio, and permits the diluted sampled to be dispensed into the assay apparatus. The collector-diluter-dispenser serves to minimize the amount of equipment and steps required to prepare a diluted sample for testing. Thus the collector-diluter-dispenser apparatus serves to expedite the entire assay procedure and decrease the risk of error.

The following example is offered by way of illustration and not by way of limitation.

EXAMPLE

HTLV-½ STAT Test

A diagnostic test employing the subject invention is provided for in a cartridge form called the HTLV-½ STAT test. The cartridges are provided in a kit form, including all reagents required for the performance of an assay, collector-diluter-dispensers, and a tray for holding multiple cartridges.

The HTLV-½ STAT test is a rapid qualitative immunoassay for the detection of IgG antibodies to HTLV-1 and HTLV-2 in human serum, plasma, or whole blood. The test is designed primarily for use with fresh samples.

Principle of the Assay

The HTLV-½-STAT test is an easy to use panel test which allows the detection on a single clinical sample of anti-HTLV-1 and anti-HTLV-2 antibodies in comparison with built in positive and negative controls.

Several reactive membrane regions offset by non-porous dividers ("miniwells") are divided out on a test cartridge.

These miniwells consist, from top to bottom, of the positive and negative procedural controls and of an HTLV-1/HTLV-2 viral lysate antigen circle and of an HTLV-1/HTLV-2 synthetic peptide circle. The first miniwell is separated from the second miniwell by a red non-porous divider. The second and third miniwells are separated by a yellow divider. Similarly, the third and fourth miniwells are separated by a white divider.

A single dilution of clinical sample is added to the cartridge. Bound IgG is detected by means of an immunoenzymatic reaction (including an amplification step to provide a high sensitivity) which results in the development of a stable blue color on the membrane.

A distinctive double ring pattern ensures an easy and sensitive reading of the test results. The positive procedural control verifies that the clinical sample was not omitted, that all reagents were active, and that the test was performed correctly.

The negative procedural control allows an easy differentiation of low positive specimens versus negative specimens.

No specialized equipment is required to perform or read the test. Results are obtained within a few minutes. The format of the test is adapted to both single testing and batch testing using a standard multichannel micropipette.

Kit Components

1. HTLV-STAT cartridges ready for use.
2. LYOPHILIZED REAGENT (A) (0.1 M PBS pH 7.4 with 1% casein (w/v), 0.1% Tween 20, v/v)
3. Collector-diluter-dispensers
4. LYOPHILIZED REAGENT (C) (anti-human IgG Biotin conjugate diluted 1:100 in 0.1 M PBS pH 7.4 with 1% casein (w/v)
5. LYOPHILIZED REAGENT (D) (alkaline phosphatase streptavidin conjugate diluted 1:100 in 0.1 M borate pH 8 with 1% BSA, w/v).
6. WASH SOLUTION/BUFFER DILUENT (E) (0.05 M borate pH 8 with 0.01% thimerosal w/v).
7. CHROMOGENIC SUBSTRATE (F) Bromochloroindoxyl phosphate solution.
8. STOPPING SOLUTION (G) 0.2 M phosphate pH 6.
9. ANTI-HTLV-1 POSITIVE SERUM (INACTIVATED) (I)
10. STAT TEST UNIT HOLDING TRAY (Using a nylon filter and nylon nib (Nib 99356) a solution of HTLV-1peptide at 1 mg/ml DMSO is diluted 1:40 into 0.1 M acetate, pH 4. The nib is attached to a reservoir and the nib pressed down onto the nylon filter until liquid diffuses to cover the miniwell. Two nibs may be used to form two circles per miniwell.)

Directions for performing the assay are as follows:

Preparation of Reagents

Bring the reagents to room temperature before use. Reconstitute the lyophilized reagents A, C and D with 7 ml of solution E. Gently agitate the reagents to mix. Allow the reagents to sit at room temperature for a few minutes. Reagent containers are dropper-top bottles. The droppers have measuring lines for adding predetermined amounts of reagent to the assay. If batch testing is to be performed, standard multichannel (8 to 12) micropipettes may be used instead of droppers.

Assay Procedure

Label the necessary number of HTLV-STAT cartridges (one for each specimen). Place the cartridges (1 to 12) in the device tray.

Add 400 $\mu$l of reconstituted reagent A (using the dropper A filled up to the measuring line) to the HTLV-STAT cartridge. Allow to drain completely.

Collect and dilute the specimen using a collector-diluter-dispenser (CDD). (The CDD has a nib with a capacity of about 30 $\mu$l and a vial with 1 ml of 0.1 M carbonate/bicarbonate buffer, 1% casein, 0.1% Tween-20, 0.01% thimerosal, pH 9.5.)

Using the collector-diluter-dispenser, add 8 drops of diluted specimen to the cartridge. Wait 3 to 5 minutes.

Add 200 $\mu$l of reconstituted reagent C to the cartridge. Allow to drain completely.

Add 200 $\mu$l of reconstituted reagent D to the cartridge. Allow to drain completely.

Add 1 ml of wash solution E to the cartridge. Allow to drain completely.

Add 200 $\mu$l (8 drops) of chromogenic substrate F to the cartridge.

Wait 3 minutes. Read the results.

Optional: Read the results again 5 to 10 minutes later. Add 200 $\mu$l of stopping solution G to the cartridge.

Interpretation of Results

Validation of the test: blue rings are seen in the first miniwell (positive procedural control) below the red divider. The second miniwell (second miniwell; below the first yellow divider) shows either nothing or light blue rings.

Blue rings in the third and fourth miniwells (between the yellow and the white divider) darker than in the second miniwell indicate a positive result for anti-HTLV-1 or anti-HTLV-2 antibodies.

Blue color development in all the miniwells indicates a test malfunction.

Blue rings in the third miniwell with no blue rings in the fourth miniwell or vice versa should be retested and confirmed using other tests.

Used cartridges can be stored desiccated after the reaction is stopped to serve as a permanent record.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A kit for performing a diagnostic assay, said kit comprising:
  (1) a collector-dilutor-dispenser device useful for processing a sample for a diagnostic assay and quantitatively measuring a sample volume, said device comprising:
    a compressible tube enclosed at one end;
    a cover mounted over the open end of said tube and comprising at least one aperture;
    a liquid medium in said tube;
    at least one frangible barrier separating said medium from said aperture; and
    at least one absorbent nib in said tube above said barrier and extending through said aperture, said nib comprising means for preventing said nib to pass through said aperture, providing substantially quantitative release of said sample into said liquid medium for allowing for quantitative determination of an analyte in said sample;
  (2) a diagnostic device for measuring an analyte which is a member of a specific binding pair, where a label is employed for said measuring which label provides for a visual detectable signal, said device comprising:
    a housing comprising an upper reservoir portion and a lower casing portion for holding at least one layer;
    in said casing in the direction of flow:
      a porous reactive filter as the floor of said reservoir component comprising a measurement circle of a member of a specific binding pair immobilized to said filter and defining a concentration gradient comprising an inner circle at an elevated concentration and an outer contiguous circle at a substantially lower concentration; and
      fluid receiving means for receiving fluid from said porous reactive filter; and
  (3) reagents for performing said assay.

2. A method for detecting the presence of an analyte in a sample, said method employing a reagent system which produces a visual signal for detecting the formation of specific binding pair member complexes, and a collector-dilutor-dispenser device useful for processing a sample for a diagnostic assay and measuring a sample volume, said device comprising:
  a compressible tube closed at one end;
  a cover mounted over the open end of said tube and comprising at least one aperture;
  a liquid medium for use in said diagnostic assay is said tube as the assay medium;
  a least one frangible barrier separating said medium from said aperture; and
  at least one absorbent nib in said tube above said barrier and extending through said aperture, said nib comprising means for preventing said nib to pass through said aperture, wherein said nib is supported by said frangible barrier and becomes at least partially immersed in said medium upon breaking of said frangible barrier, said nib being capable of absorbing a predetermined liquid volume and substantially quantitatively releasing said sample into said liquid medium; said method comprising:
    contacting said sample with said nib, wherein said nib absorbs said sample in a predetermined volume;

breaking said frangible barrier, whereby said nib is combined with said liquid medium and said sample is dispensed into said liquid medium, wherein said liquid medium optionally includes at least one reagent of said reagent system;

transferring said liquid medium through said aperture in the absence of said nib to the reservoir of a diagnostic device for measuring an analyte which is a member of a specific binding pair, said device comprising:

a housing comprising an upper reservoir portion and a lower casing portion for holding at least one layer;

in said casing in the direction of flow:

a porous reactive filter as the floor of said reservoir component comprising a measurement circle of a member of a specific binding pair immobilized to said filter and defining a concentration gradient comprising an inner circle at an elevated concentration and an outer contiguous circle at a substantially lower concentration; and fluid receiving means for receiving fluid from said porous reactive filter;

allowing said liquid medium to pass through said porous reactive filter into said fluid receiving means;

adding any additional reagents of said reagent system to said porous reactive filter; and detecting the presence of said visual signal in relation to a visual signal obtained with a sample having a known amount of analyte.

3. A method according to claim 2, wherein said member of a specific binding pair immobilized to said filter is an antibody.

4. A method according to claim 2, wherein said visual signal is as a result of production of a visual product of an enzymatic reaction.

* * * * *